(12) United States Patent
Schultz et al.

(10) Patent No.: US 6,986,789 B2
(45) Date of Patent: Jan. 17, 2006

(54) INTERVERTEBRAL IMPLANT

(75) Inventors: Robert Schultz, Tuttlingen (DE);
Stephan Lindner, Tuttlingen (DE)

(73) Assignee: Aesculap AG & Co. KG, Tuttlingen (DE)

( * ) Notice: Subject to any disclaimer, the term of this patent is extended or adjusted under 35 U.S.C. 154(b) by 0 days.

(21) Appl. No.: 10/885,428

(22) Filed: Jul. 6, 2004

(65) Prior Publication Data

US 2005/0043803 A1    Feb. 24, 2005

(30) Foreign Application Priority Data

Aug. 22, 2003   (DE) ................... 103 39 170
Oct. 16, 2003   (DE) ................... 203 13 183

(51) Int. Cl.
*A61F 2/44* (2006.01)
(52) U.S. Cl. ................................. 623/17.15
(58) Field of Classification Search ......... 623/17.11, 623/17.14, 17.15, 17.16, 17.12, 17.13
See application file for complete search history.

(56) References Cited

U.S. PATENT DOCUMENTS

| | | |
|---|---|---|
| 3,426,364 A | 2/1969 | Lumb |
| 3,867,728 A | 2/1975 | Stubstad et al. |
| 3,875,595 A | 4/1975 | Froning |
| 4,309,777 A | 1/1982 | Patil |
| 4,759,766 A * | 7/1988 | Buettner-Janz et al. .. 623/17.15 |
| 4,759,769 A | 7/1988 | Hedman et al. |
| 4,863,476 A | 9/1989 | Shepperd |
| 4,863,477 A | 9/1989 | Monson |
| 4,911,718 A | 3/1990 | Lee et al. |
| 5,002,576 A | 3/1991 | Fuhrmann et al. |
| 5,122,130 A | 6/1992 | Keller |
| 5,123,926 A | 6/1992 | Pisharodi |
| 5,236,460 A | 8/1993 | Barber |
| 5,258,031 A | 11/1993 | Salib et al. |
| 5,306,308 A | 4/1994 | Gross et al. |
| 5,314,477 A | 5/1994 | Marnay |
| 5,370,697 A | 12/1994 | Baumgartner |
| 5,401,269 A * | 3/1995 | Buttner-Janz et al. ... 623/17.15 |
| 5,425,773 A | 6/1995 | Boyd et al. |
| 5,507,816 A | 4/1996 | Bullivant |
| 5,534,030 A | 7/1996 | Navarro et al. |
| 5,556,431 A | 9/1996 | Büttner-Janz |
| 5,562,738 A | 10/1996 | Boyd et al. |
| 5,674,294 A | 10/1997 | Bainville et al. |
| 5,674,296 A | 10/1997 | Bryan et al. |
| 5,676,635 A | 10/1997 | Levin |
| 5,676,701 A | 10/1997 | Yuan et al. |
| 5,683,465 A | 11/1997 | Shinn et al. |
| 5,702,449 A | 12/1997 | McKay |
| 5,782,830 A | 7/1998 | Farris |
| 5,782,832 A | 7/1998 | Larsen et al. |

(Continued)

FOREIGN PATENT DOCUMENTS

DE          30 23 353 A1      4/1981

(Continued)

*Primary Examiner*—David H. Willse
*Assistant Examiner*—Javier G. Blanco
(74) *Attorney, Agent, or Firm*—RatnerPrestia

(57) ABSTRACT

An intervertebral implant is provided, including an upper support body including a dorsal edge, a lower support body including a dorsal edge, and a saddle joint. The saddle joint includes two pivot axes and two saddle-shaped joint surfaces in contact with one another rotated by 90° in relation to one another. The upper and lower support bodies are supported pivotably in relation to one another via the saddle joint.

17 Claims, 8 Drawing Sheets

U.S. PATENT DOCUMENTS

| | | | |
|---|---|---|---|
| 5,824,094 A | 10/1998 | Serhan et al. | |
| 5,827,328 A | 10/1998 | Buttermann | |
| 5,865,846 A | 2/1999 | Bryan et al. | |
| 5,888,226 A | 3/1999 | Rogozinski | |
| 5,888,227 A | 3/1999 | Cottle | |
| 5,893,889 A | 4/1999 | Harrington | |
| 5,989,291 A | 11/1999 | Ralph et al. | |
| 6,001,130 A | 12/1999 | Bryan et al. | |
| 6,019,793 A | 2/2000 | Perren et al. | |
| 6,039,763 A * | 3/2000 | Shelokov | 623/17.16 |
| 6,063,121 A | 5/2000 | Xavier et al. | |
| 6,083,225 A | 7/2000 | Winslow et al. | |
| 6,113,637 A | 9/2000 | Gill et al. | |
| 6,113,639 A | 9/2000 | Ray et al. | |
| 6,127,597 A | 10/2000 | Beyar et al. | |
| 6,139,579 A | 10/2000 | Steffee et al. | |
| 6,156,067 A | 12/2000 | Bryan et al. | |
| 6,162,252 A | 12/2000 | Kuras et al. | |
| 6,176,881 B1 | 1/2001 | Schär et al. | |
| 6,200,322 B1 | 3/2001 | Branch et al. | |
| 6,210,442 B1 | 4/2001 | Wing et al. | |
| 6,231,609 B1 | 5/2001 | Mehdizadeh | |
| 6,296,664 B1 | 10/2001 | Middleton | |
| 6,348,071 B1 | 2/2002 | Steffee et al. | |
| 6,368,350 B1 * | 4/2002 | Erickson et al. | 623/17.14 |
| 6,395,032 B1 | 5/2002 | Gauchet | |
| 6,419,706 B1 | 7/2002 | Graf | |
| 6,443,987 B1 | 9/2002 | Bryan | |
| 6,443,990 B1 | 9/2002 | Aebi et al. | |
| 6,468,310 B1 | 10/2002 | Ralph et al. | |
| 6,517,580 B1 | 2/2003 | Ramadan et al. | |
| 6,524,341 B2 | 2/2003 | Läng et al. | |
| 6,527,804 B1 | 3/2003 | Gauchet et al. | |
| 6,527,806 B2 | 3/2003 | Ralph et al. | |
| 6,533,818 B1 | 3/2003 | Weber et al. | |
| 6,540,785 B1 | 4/2003 | Gill et al. | |
| 6,558,424 B2 | 5/2003 | Thalgott | |
| 6,562,072 B1 | 5/2003 | Fuss et al. | |
| 6,572,653 B1 | 6/2003 | Simonson | |
| 6,575,899 B1 | 6/2003 | Foley et al. | |
| 6,579,320 B1 | 6/2003 | Gauchet et al. | |
| 6,579,321 B1 | 6/2003 | Gordon et al. | |
| 6,582,466 B1 | 6/2003 | Gauchet | |
| 6,582,468 B1 | 6/2003 | Gauchet | |
| 6,607,558 B2 | 8/2003 | Kuras | |
| 6,610,092 B2 | 8/2003 | Ralph et al. | |
| 6,613,090 B2 | 9/2003 | Eckhof et al. | |
| 6,626,943 B2 | 9/2003 | Eberlein et al. | |
| 6,645,248 B2 | 11/2003 | Casutt | |
| 6,645,249 B2 | 11/2003 | Ralph et al. | |
| 6,656,224 B2 | 12/2003 | Middleton | |
| 6,666,889 B1 | 12/2003 | Commarmond | |
| 6,669,730 B2 | 12/2003 | Ralph et al. | |
| 6,669,732 B2 | 12/2003 | Serhan et al. | |
| 6,673,113 B2 | 1/2004 | Ralph et al. | |
| 6,682,562 B2 | 1/2004 | Viart et al. | |
| 6,706,068 B2 * | 3/2004 | Ferree | 623/17.11 |
| 6,719,796 B2 | 4/2004 | Cohen et al. | |
| 6,723,097 B2 | 4/2004 | Fraser et al. | |
| 6,723,127 B2 | 4/2004 | Ralph et al. | |
| 6,726,720 B2 | 4/2004 | Ross et al. | |
| 6,733,532 B1 | 5/2004 | Gauchet et al. | |
| 6,736,850 B2 | 5/2004 | Davis | |
| 6,740,117 B2 | 5/2004 | Ralph et al. | |
| 6,740,118 B2 | 5/2004 | Eisermann et al. | |
| 6,740,119 B2 | 5/2004 | Ralph et al. | |
| 6,758,861 B2 | 7/2004 | Ralph et al. | |
| 6,764,515 B2 | 7/2004 | Ralph et al. | |
| 6,770,094 B2 | 8/2004 | Fehling et al. | |
| 6,770,095 B2 | 8/2004 | Grinberg et al. | |
| 6,793,678 B2 | 9/2004 | Hawkins | |
| 6,802,867 B2 | 10/2004 | Manasas et al. | |
| 6,827,740 B1 | 12/2004 | Michelson | |
| 2001/0016773 A1 | 8/2001 | Serhan et al. | |
| 2002/0035400 A1 | 3/2002 | Bryan et al. | |
| 2002/0107573 A1 | 8/2002 | Steinberg | |
| 2002/0111681 A1 | 8/2002 | Ralph et al. | |
| 2003/0009223 A1 | 1/2003 | Fehling et al. | |
| 2003/0014112 A1 | 1/2003 | Ralph et al. | |
| 2003/0040802 A1 | 2/2003 | Errico et al. | |
| 2003/0065395 A1 | 4/2003 | Ralph et al. | |
| 2003/0069586 A1 | 4/2003 | Errico et al. | |
| 2003/0069643 A1 | 4/2003 | Ralph et al. | |
| 2003/0074066 A1 | 4/2003 | Errico et al. | |
| 2003/0074067 A1 | 4/2003 | Errico et al. | |
| 2003/0074068 A1 | 4/2003 | Errico et al. | |
| 2003/0074069 A1 | 4/2003 | Errico et al. | |
| 2003/0074070 A1 | 4/2003 | Errico et al. | |
| 2003/0074071 A1 | 4/2003 | Errico et al. | |
| 2003/0074072 A1 | 4/2003 | Errico et al. | |
| 2003/0074073 A1 | 4/2003 | Errico et al. | |
| 2003/0074074 A1 | 4/2003 | Errico et al. | |
| 2003/0078590 A1 | 4/2003 | Errico et al. | |
| 2003/0078663 A1 | 4/2003 | Ralph et al. | |
| 2003/0078666 A1 | 4/2003 | Ralph et al. | |
| 2003/0135277 A1 | 7/2003 | Bryan et al. | |
| 2003/0176923 A1 | 9/2003 | Keller et al. | |
| 2003/0187454 A1 | 10/2003 | Gill et al. | |
| 2003/0187506 A1 | 10/2003 | Ross et al. | |
| 2003/0220691 A1 | 11/2003 | Songer et al. | |
| 2003/0229355 A1 | 12/2003 | Keller | |
| 2003/0229358 A1 | 12/2003 | Errico et al. | |
| 2003/0233146 A1 | 12/2003 | Grinberg et al. | |
| 2003/0236520 A1 | 12/2003 | Lim et al. | |
| 2003/0236571 A1 | 12/2003 | Ralph et al. | |
| 2004/0002761 A1 | 1/2004 | Rogers et al. | |
| 2004/0002762 A1 | 1/2004 | Hawkins | |
| 2004/0010316 A1 | 1/2004 | William et al. | |
| 2004/0024462 A1 * | 2/2004 | Ferree et al. | 623/17.14 |
| 2004/0034420 A1 | 2/2004 | Errico et al. | |
| 2004/0034421 A1 | 2/2004 | Errico et al. | |
| 2004/0034422 A1 | 2/2004 | Errico et al. | |
| 2004/0034424 A1 | 2/2004 | Errico et al. | |
| 2004/0034425 A1 | 2/2004 | Errico et al. | |
| 2004/0034426 A1 | 2/2004 | Errico et al. | |
| 2004/0059318 A1 | 3/2004 | Zhang et al. | |
| 2004/0073310 A1 | 4/2004 | Moumene et al. | |
| 2004/0073312 A1 | 4/2004 | Eisermann et al. | |
| 2004/0078079 A1 | 4/2004 | Foley | |
| 2004/0083000 A1 | 4/2004 | Keller et al. | |
| 2004/0093088 A1 | 5/2004 | Ralph et al. | |
| 2004/0098130 A1 | 5/2004 | Ralph et al. | |
| 2004/0098131 A1 | 5/2004 | Bryan et al. | |
| 2004/0102849 A1 | 5/2004 | Ralph et al. | |
| 2004/0111156 A1 | 6/2004 | Ralph et al. | |
| 2004/0117021 A1 | 6/2004 | Biedermann et al. | |
| 2004/0117022 A1 | 6/2004 | Marnay et al. | |
| 2004/0133281 A1 * | 7/2004 | Khandkar et al. | 623/17.16 |
| 2004/0143331 A1 | 7/2004 | Errico et al. | |
| 2004/0143332 A1 | 7/2004 | Krueger et al. | |
| 2004/0148027 A1 | 7/2004 | Errico et al. | |
| 2004/0158325 A1 | 8/2004 | Errico et al. | |
| 2004/0158328 A1 | 8/2004 | Elsermann | |
| 2004/0167534 A1 | 8/2004 | Errico et al. | |
| 2004/0167536 A1 | 8/2004 | Errico et al. | |
| 2004/0167537 A1 | 8/2004 | Errico et al. | |
| 2004/0167626 A1 | 8/2004 | Geremakis et al. | |
| 2004/0193158 A1 | 9/2004 | Lim et al. | |
| 2004/0220582 A1 | 11/2004 | Keller | |
| 2004/0220668 A1 | 11/2004 | Elsermann et al. | |
| 2004/0220670 A1 | 11/2004 | Elsermann et al. | |
| 2004/0220677 A1 | 11/2004 | Delfosse et al. | |
| 2004/0225362 A1 | 11/2004 | Richelsoph | |
| 2004/0225363 A1 | 11/2004 | Richelsoph | |

| | | | |
|---|---|---|---|
| 2004/0225364 A1 | 11/2004 | Richelsoph et al. | |
| 2004/0225365 A1 | 11/2004 | Elsermann et al. | |
| 2004/0225366 A1 | 11/2004 | Elsermann et al. | |
| 2004/0243238 A1 | 12/2004 | Arnin et al. | |
| 2004/0243240 A1 | 12/2004 | Beaurain et al. | |
| 2004/0249462 A1 | 12/2004 | Huang | |
| 2005/0043803 A1 | 2/2005 | Schultz et al. | |

FOREIGN PATENT DOCUMENTS

| | | |
|---|---|---|
| DE | 697 22 244 T2 | 5/1998 |
| DE | 197 10 392 C1 | 7/1999 |
| DE | 198 16 832 C1 | 1/2000 |
| DE | 101 52 567 A1 | 5/2003 |
| DE | 203 10 432 U1 | 10/2003 |
| DE | 203 10 433 U1 | 10/2003 |
| DE | 203 11 400 U1 | 11/2003 |
| DE | 203 13 183 U1 | 11/2003 |
| DE | 203 15 611 U1 | 1/2004 |
| DE | 203 15 613 U1 | 1/2004 |
| DE | 20 2004 009 542 U1 | 9/2004 |
| DE | 20 2004 014 119 U1 | 12/2004 |
| EP | 0 471 821 B1 | 2/1992 |
| EP | 0 282 161 B1 | 8/1992 |
| EP | 0 560 140 B1 | 9/1993 |
| EP | 0 560 141 B1 | 9/1993 |
| EP | 0 634 157 B1 | 1/1995 |
| EP | 0 747 025 B1 | 12/1996 |
| EP | 1 002 500 A1 | 5/2000 |
| EP | 1 344 507 A1 | 3/2002 |
| EP | 1 344 508 A1 | 3/2002 |
| EP | 1250898 A1 | 10/2002 |
| EP | 0 948 299 B1 | 5/2003 |
| EP | 1 374 808 A1 | 1/2004 |
| EP | 1 401 360 A1 | 3/2004 |
| EP | 1124509 B1 | 3/2004 |
| EP | 1 421 922 A1 | 5/2004 |
| EP | 1 475 059 A2 | 11/2004 |
| FR | 2 694 882 | 2/1994 |
| FR | 2730159 A1 * | 8/1996 |
| FR | 2 799 116 | 4/2001 |
| FR | 2824261 A1 * | 11/2002 |
| JP | 06178787 A | 6/1994 |
| WO | WO 95/26697 A1 | 10/1995 |
| WO | WO-9911203 | 3/1999 |
| WO | WO 00/23015 | 4/2000 |
| WO | WO 00/53127 | 9/2000 |
| WO | WO 00/64385 A1 | 11/2000 |
| WO | WO 01/01893 A1 | 1/2001 |
| WO | WO 01/01895 A1 | 1/2001 |
| WO | WO 01/19295 | 3/2001 |
| WO | WO-0118931 A1 | 3/2001 |
| WO | WO 01/64140 | 9/2001 |
| WO | WO 01/83786 A2 | 12/2001 |
| WO | WO 01/93785 A2 | 12/2001 |
| WO | WO 02/080818 A1 | 10/2002 |
| WO | WO 02/089701 A2 | 11/2002 |
| WO | WO 03/003952 A1 | 1/2003 |
| WO | WO 03/007779 | 1/2003 |
| WO | WO 03/007780 A2 | 1/2003 |
| WO | WO 03/007780 A3 | 1/2003 |
| WO | WO 03/039400 A2 | 5/2003 |
| WO | WO 03/047472 A1 | 6/2003 |
| WO | WO 03/075803 A1 | 9/2003 |
| WO | WO 03/075804 | 9/2003 |
| WO | WO 03/084449 A1 | 10/2003 |
| WO | WO 03/094806 | 11/2003 |
| WO | WO 03/099172 A1 | 12/2003 |
| WO | WO 2004/016205 A2 | 2/2004 |
| WO | WO 2004/019828 A1 | 3/2004 |
| WO | WO 2004026186 A1 * | 4/2004 |
| WO | WO 2004/039285 A2 | 5/2004 |
| WO | WO 2004/041129 A1 | 5/2004 |
| WO | WO 2004/041131 A2 | 5/2004 |
| WO | WO 2004/054475 A1 | 7/2004 |
| WO | WO 2004/054476 A1 | 7/2004 |
| WO | WO 2004/054478 A1 | 7/2004 |
| WO | WO 2004/054480 A1 | 7/2004 |
| WO | WO 2004/073561 A1 | 9/2004 |
| WO | WO 2004/084774 A1 | 10/2004 |

* cited by examiner

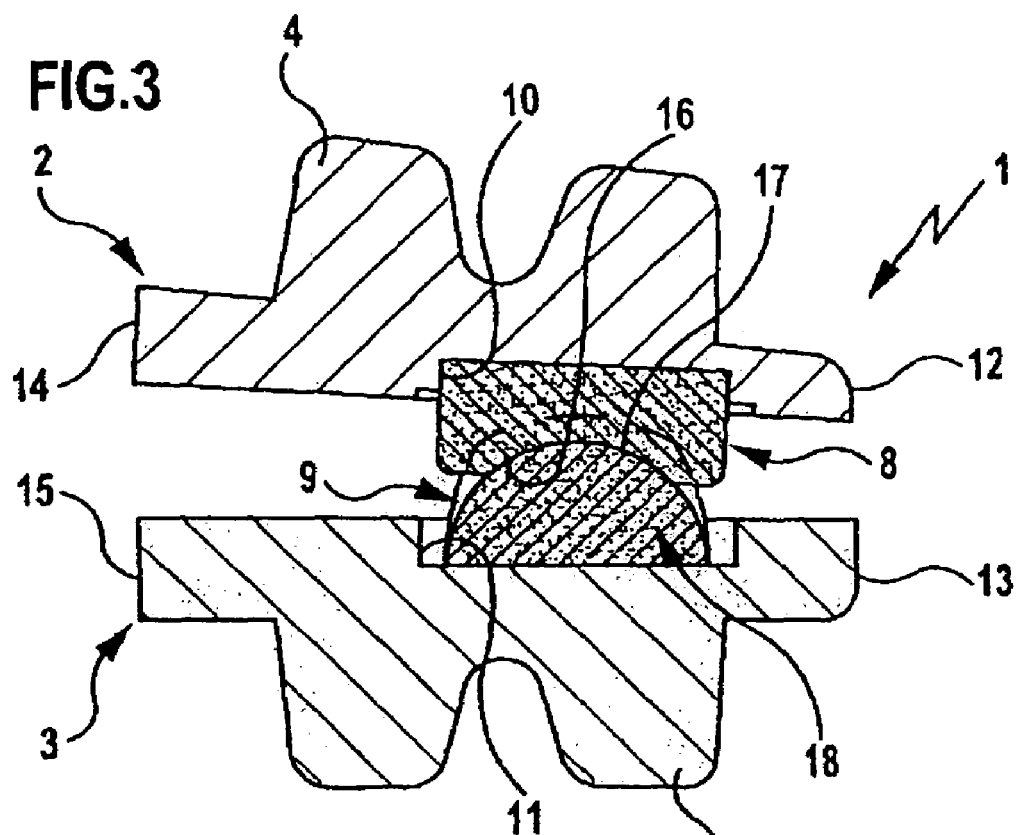
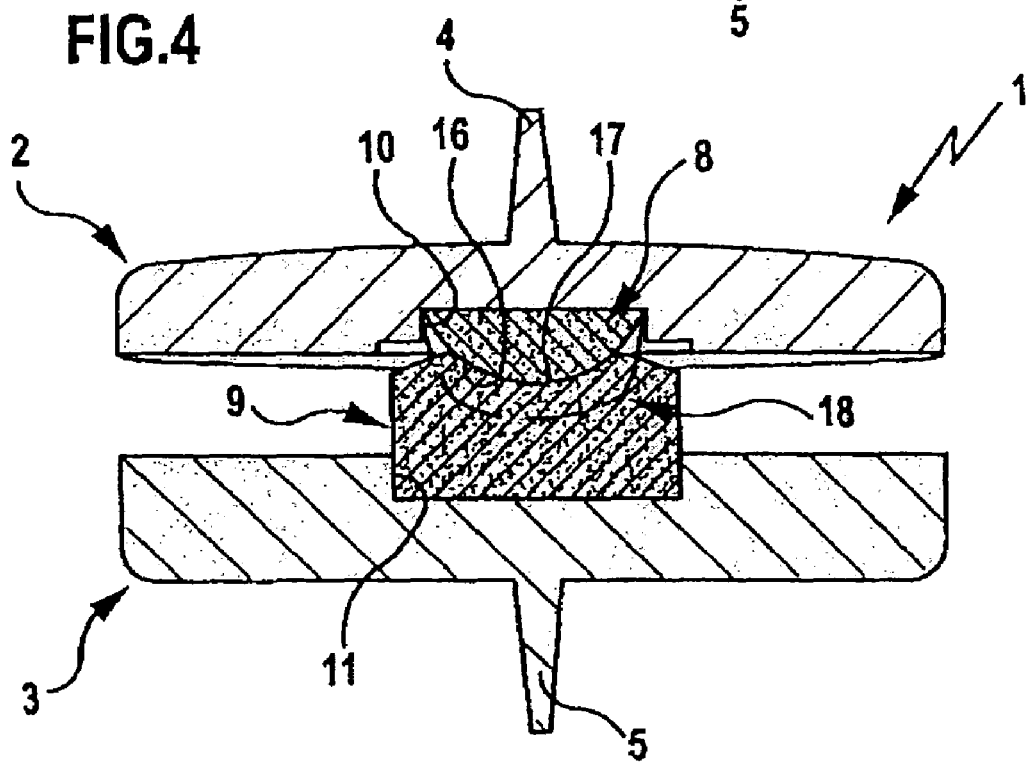

INTERVERTEBRAL IMPLANT

This application is related to and claims the benefit of German Utility Model No. 203 13 183.5 entitled Intervertebral Implant issued on Oct. 16, 2003, and German Patent Application No. 103 39 170.3 filed Aug. 22, 2003.

FIELD OF THE INVENTION

The present invention pertains to an intervertebral implant with which the original height of the intervertebral disk can be restored, e.g., in case of degeneratively altered intervertebral disks, and the function can be preserved at the same time.

BACKGROUND OF THE INVENTION

Intervertebral implants may be based on a ball and socket joint, i.e., they make pivotability possible in the same way in all directions. For example, an intervertebral disk prosthesis with two metallic end plates and an intermediate part made of polyethylene, in which a convex bearing surface slides on a concave surface, is described in WO 01/01893. In this prosthesis, the rotation center is located centrally in the middle between the anterior and posterior edges of the support bodies designed as metal plates. An intervertebral disk prosthesis in which the rotation center is displaced in the dorsal direction is described in U.S. Pat. No. 5,258,031.

There remains a need for an improved intervertebral implant of the type described such that it is optimized in terms of wear, kinematics, and load distribution.

SUMMARY OF THE INVENTION

The present invention pertains to an intervertebral implant with an upper support body and a lower support body, which are supported at each other via a joint in such a way that they are pivotable in relation to one another. This implant is used as a replacement for an intervertebral disk, and the original height of the intervertebral disk can be restored by means of this implant while the function is preserved at the same time.

The joint is designed as a saddle joint, in which two saddle-shaped joint surfaces are in contact with one another, rotated by 90° in relation to one another.

Consequently, each of the two saddle-shaped joint surfaces has a convex contour in one direction and a concave contour in the direction extending at right angles thereto, and the vertex of the convex contour and the lowest point of the concave contour coincide. The joint surfaces are consequently curved in one direction opposite the curvature in a direction extending transversely thereto. The two saddle-shaped joint surfaces thus designed are rotated by 90° in relation to one another around a perpendicular axis of the intervertebral implant, so that pivoting or rotation of the joint surfaces around two axes that are at right angles to one another, which are in the plane of the intervertebral space, is possible.

While the centers of the pivoting movement around all axes coincide in a ball and socket joint, the centers of the pivoting movement around mutually perpendicular axes in a saddle joint are different. Thus, the fulcrum for flexion/extension is in the vicinity of the lower support body in a preferred embodiment, whereas the fulcrum for the lateral flexion is in the vicinity of the upper support body. Thus, such a saddle joint comes closer to the physiological conditions of the normal intervertebral disk than a ball and socket joint that has only one center for all rotary movements.

It is favorable if one joint surface is directed in the anterior-posterior direction and the other in the lateral direction.

Furthermore, it is advantageous if the saddle joint is arranged between the middle of the support bodies and the dorsal edge of the support bodies, so that the pivoting movement takes place around centers that are displaced in the dorsal direction.

It is especially advantageous if the joint surfaces consist of a ceramic, because such articulating surfaces are not subject to wear of any significance. The problem of creep under load, which cannot be avoided in case of the use of polyethylene as a joint surface material, is also eliminated with such joint surfaces.

It is also advantageous in the case of the use of ceramic that smaller dimensions can be selected for the joint components because of the very high compressive strength of the ceramic, and during the flexion/extension movement, these smaller radii reduce the translational motion superimposed to this movement. It is advantageous, for example, if the radius of the joint surfaces is between 4 mm and 7 mm and preferably equals about 5 mm. Translational motion[s] amounting to less than 2 mm during a full extension of about 14° can thus be achieved.

Provisions may be made in a preferred embodiment for the support body and the joint surface to be made of ceramic in one piece.

Provisions are made in another embodiment for the joint surfaces to be part of a joint body, which is inserted into the support body. The joint body can be inserted into the support body without clearance in this case.

For example, the joint body may be held in the support body by means of a conical clamping, and the support body can be shrunk onto the joint body, or the joint body can be fixed at the support body by means of locking screws or by means of elastic intermediate elements.

It is especially advantageous if at least one of the joint bodies is rotatable in relation to the support body receiving it around an axis of rotation extending at right angles to the two pivot axes of the saddle joint. There is a limitation to two pivot axes in a saddle joint, and the joint surfaces are only in a punctiform contact with one another during rotation around the axis of rotation extending at right angles to these two pivot axes, and they lead as a result to an increase in the distance between the two support bodies. To avoid this, at least one of the joint bodies is designed such that it is rotatable in relation to its support body, so that rotation around all three mutually perpendicular pivot axes or axes of rotation becomes possible in this embodiment.

Provisions are made in a first preferred embodiment for the rotatable joint body to be received rotatably in a rotationally symmetrical recess of the support body.

In another embodiment, the rotatable joint body has a multipart design with a bearing part held rigidly in the support body and with a joint surface part rotatable around the axis of rotation.

It is advantageous in these embodiments if a layer made of a low-friction and/or wear-reducing material, for example, a ceramic layer, is arranged between the joint body and the support body (designated by reference numeral 24 in FIG. 9) and between the bearing part and the joint surface part (designated by reference numeral 26 in FIG. 9). It is ensured hereby that the friction is reduced and the wear is diminished in the contact area of the parts that are rotatable in relation to one another.

In a preferred embodiment, the bearing part and the joint surface part may be connected with one another rotatably via a central bearing journal.

Provisions are made in another preferred embodiment for the joint surface part to be received rotatably in a bearing shell of the bearing part.

In a modified type of embodiment, the support body may consist of a metal, especially titanium, a titanium alloy, or a chromium-cobalt alloy.

The use of special plastics for the support body, e.g., the use of polyether ether ketone (PEEK™ manufactured by Victrex® PLC of the United Kingdom), is also favorable; such a plastic is transparent to X-rays and makes possible a trouble-free observation of the operating area by means of X-rays.

BRIEF DESCRIPTION OF THE DRAWINGS

FIG. 3 shows a sectional view of the implant according to FIG. 1 in a sagittal plane;

FIG. 4 shows a sectional view of the implant according to FIG. 1 in a frontal plane;

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

Figure 1:
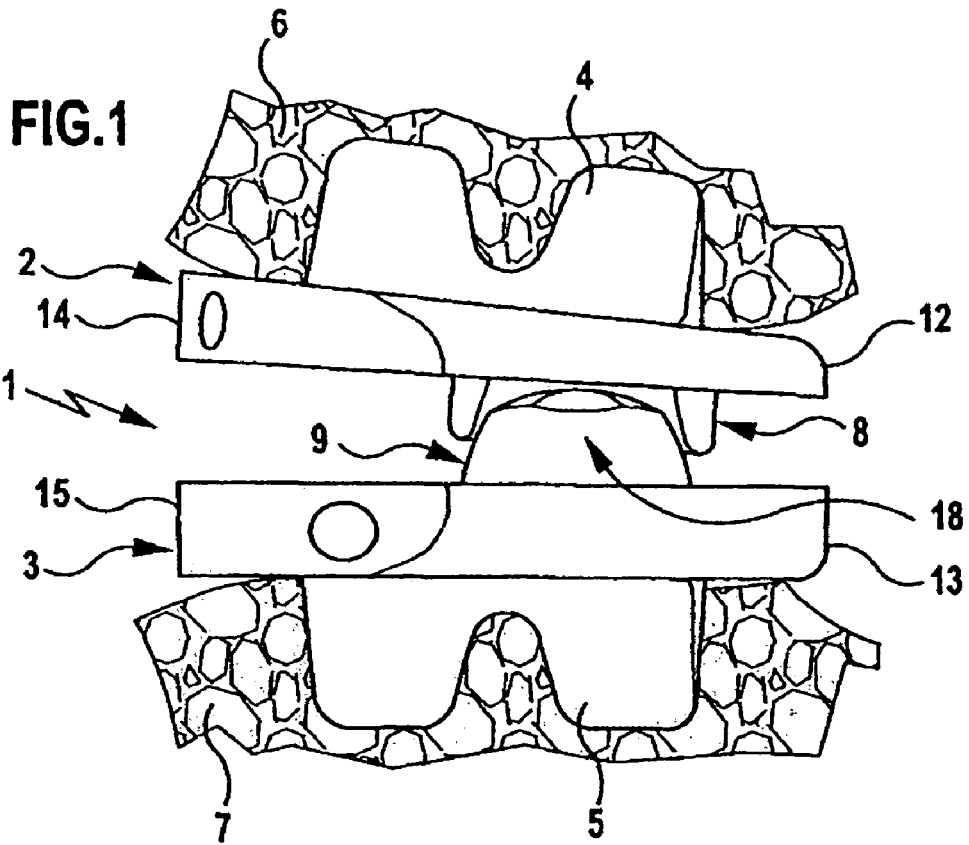
FIG. 1 shows a side view of an intervertebral implant with a saddle joint.
Figure 2:
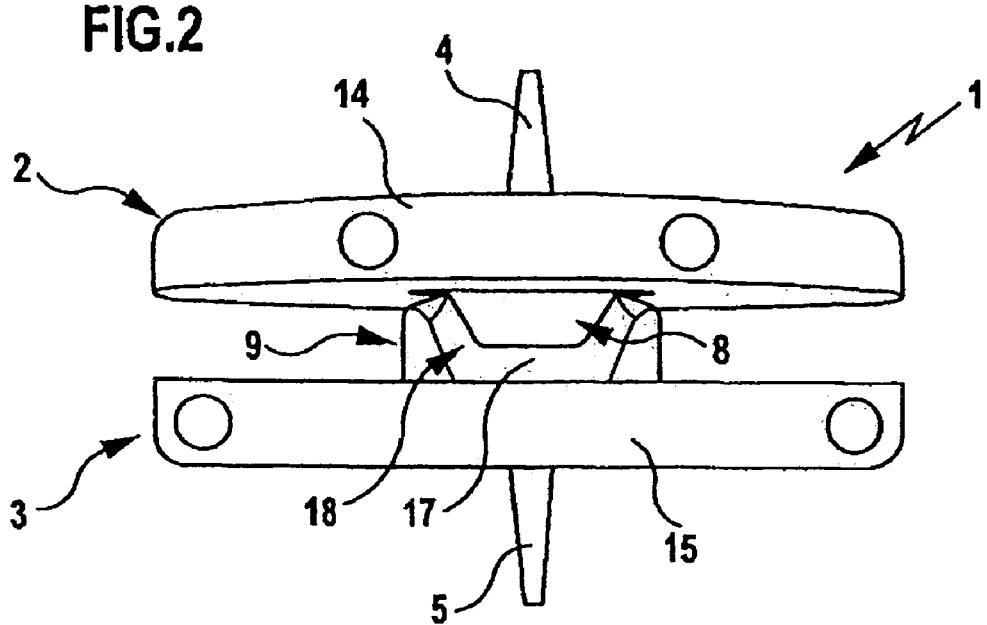
FIG. 2 shows a front view of the implant according to FIG. 1.
Figure 5:
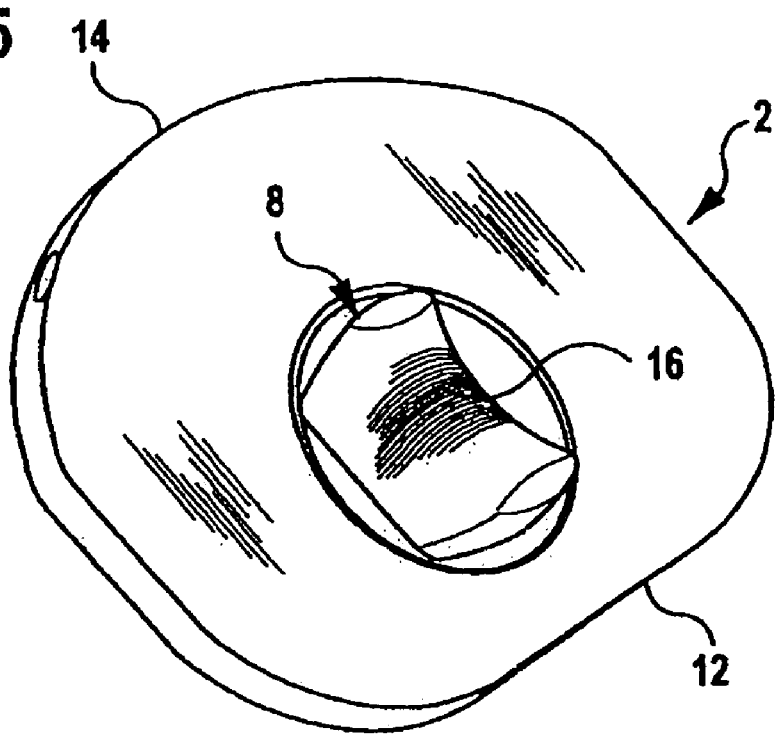
FIG. 5 shows an isometric view of the upper support body with the saddle joint surface.
Figure 6:
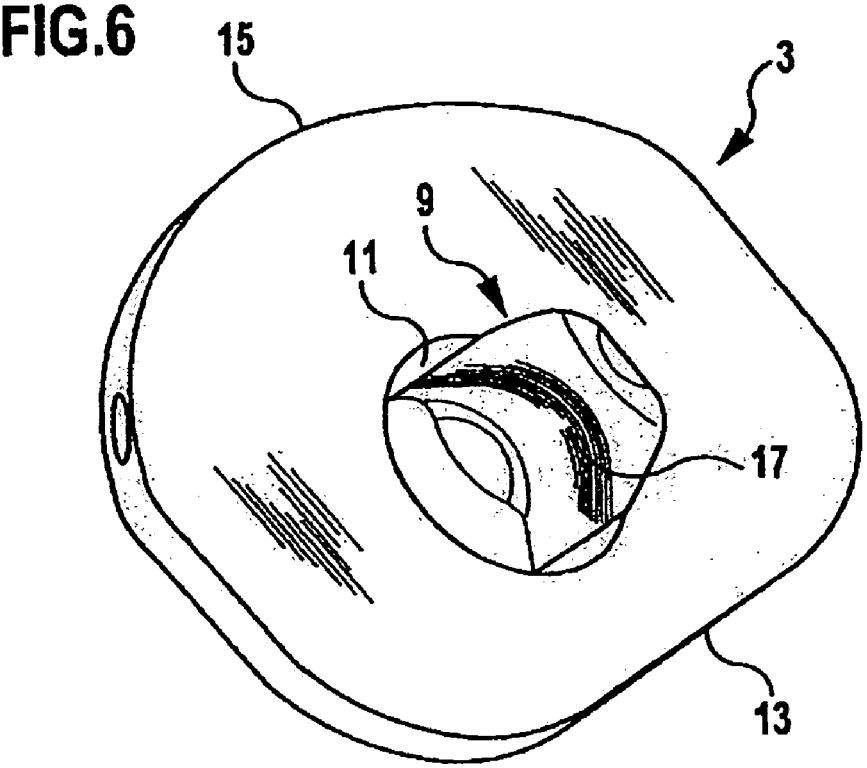
FIG. 6 shows an isometric view of the lower support body with the saddle joint surface.

The intervertebral implant 1 shown in the drawings comprises two plate-like support bodies 2, 3, which preferably consist of titanium or a titanium alloy, or another metal that is compatible with the body, and carry respective, perpendicularly projecting anchoring surfaces 4 and 5 on their sides facing away from each other. As shown in FIG. 1, the plate-like support bodies 2, 3 are placed on the underside and the top sides of two adjacent vertebral bodies 6 and 7, and the anchoring surfaces 4, 5 immerse into the vertebral bodies 6 and 7, respectively.

On their sides facing each other, the two support bodies 2, 3 carry a respective joint body 8 and 9, which are supported at each other and permit a pivoting movement of the two support bodies 2, 3.

The joint bodies 8, 9 consist of ceramic in the exemplary embodiment shown, and are inserted into a respective recess 10 and 11 of the corresponding support body 2, 3, as shown in FIG. 3. The recesses 10, 11 are not arranged in the middle of the support bodies 2, 3, but are displaced in the direction of the dorsal edge 12, 13 of the support bodies 2, 3, so that the centers of the recesses 10, 11 are at a distance from the ventral edges 14, 15 of the support bodies 2, 3 that is twice the distance from the dorsal edge 12, 13.

Both joint bodies 8, 9 form a joint surface 16 and 17, respectively, and the two joint bodies 8, 9 are supported at each other via these joint surfaces 16, 17. Each of these joint surfaces 16, 17 is designed as a saddle-shaped joint surface, i.e., this joint surface is bent convexly in one direction and concavely in the direction extending at right angles to that direction, and the lowest point of the concave contour coincides with the highest point of the convex contour. The joint bodies 8, 9 are rotated by 90° in relation to one another, so that the saddle joint 18 formed by these joint bodies 8, 9 permits pivoting in two mutually perpendicular directions that are parallel to the lower support body 3. The arrangement is selected here to be such that these pivot axes extend in parallel to the anterior-posterior direction and in parallel to the lateral direction.

The saddle joint 18 permits the pivoting of the two support bodies 2, 3 in relation to one another, so that both lateral flexion and extension/flexion of the adjacent vertebral bodies 6, 7 are possible, but such a saddle joint 18 prevents the rotation of the two support bodies 2, 3 around an axis of rotation extending at right angles to the plate-like support body 2, 3 if the two joint bodies 8, 9 are rigidly connected with their respective support bodies 2, 3.

Such a rigid connection may be provided, for example, the joint bodies 8, 9 may be fixed in the support bodies 2, 3 by additional clamping elements not shown in the drawings or by shrinking the support bodies onto the joint bodies or according to other fixing methods.

Figure 7:
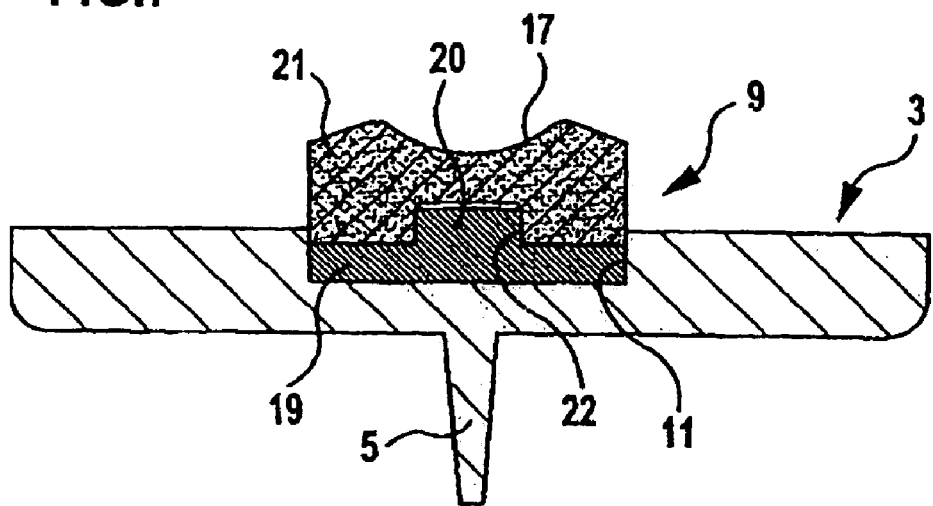
FIG. 7 shows a sectional view in the frontal plane in a support body with a two-part joint body and pivot mounting.

However, provisions are made in a preferred exemplary embodiment for at least one of the joint bodies 8, 9 to be rotatable in relation to its support body 2 or 3 around a perpendicular axis of rotation, i.e., around an axis of rotation that extends transversely to the pivot axes that are formed by the saddle joint 18. This can be achieved simply by the joint body being freely rotatable in the corresponding recess of the support body, but provisions may also be made for the use of special embodiments of the joint body for this, as is shown, for example, in FIGS. 7 and 8. The lower joint body 9 has a two-part design in the exemplary embodiment according to FIG. 7, comprising a bearing part 19 inserted into the recess 11, rotating in unison, with a central bearing journal 20 and a joint surface part 21 placed flatly on this bearing part 19 with a central bearing opening 22 adapted to the bearing journal 20. The joint surface part 21 is thus rotatable on the bearing part 19 around the axis of rotation defined by the bearing journal 20.

Figure 8:
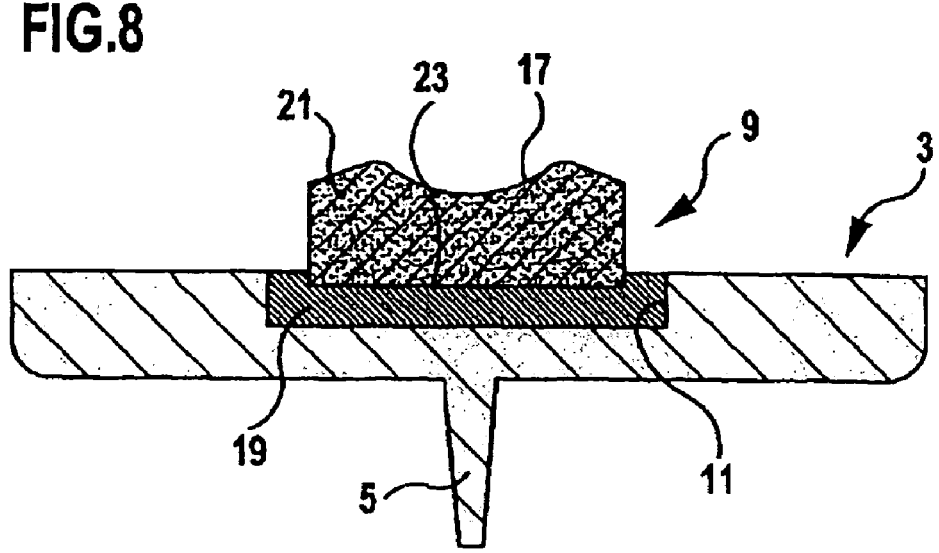
FIG. 8 shows a view similar to that in FIG. 7 with a bearing shell mounting.
Figure 9:
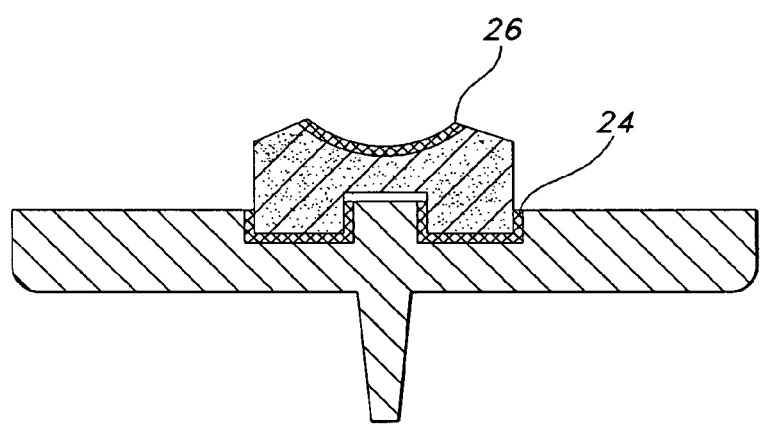
FIG. 9 shows a sectional view in the frontal place in a support body with a low-friction and/or wear-reducing material arranged between the joint body and the support body and between the bearing part and the joint surface part.

A central bearing journal is missing in the exemplary embodiment according to FIG. 8, in which parts that correspond to each other are designated by the same reference numbers, but a rotationally symmetrical bearing shell 23, which receives the joint surface part 21 and supports it rotatably around the axis of rotation, is formed in the bearing part 19, instead.

Biocompatible metals, especially titanium alloys or chromium-cobalt alloys, are preferably used as the material for the above-described parts. As an alternative, components may be made of plastic, especially from PEEK™, which is a polymer (polyether ether ketone) manufactured by Victrex® PLC of the United Kingdom. PEEK™ is transparent to X-rays, which leads to a great advantage in postoperative X-ray diagnostics with CTs or nuclear spin tomography, because, unlike metals, the plastic does not cause any artifacts (i.e., obstructions) in the X-ray image.

To minimize wear, components may be made of ceramic. Such ceramic components are manufactured with corresponding precision such that the wear nearly equals zero. A further advantage of a ceramic-on-ceramic bearing is that the problem of creep under load, which is peculiar to polyethylene, is absent. Since ceramic material has a substantially higher compressive strength and dimensional stability than polyethylene, dimensions may be reduced. The forced translational motion superimposed to the flexion/extension movement decreases as a result.

Figure 10:
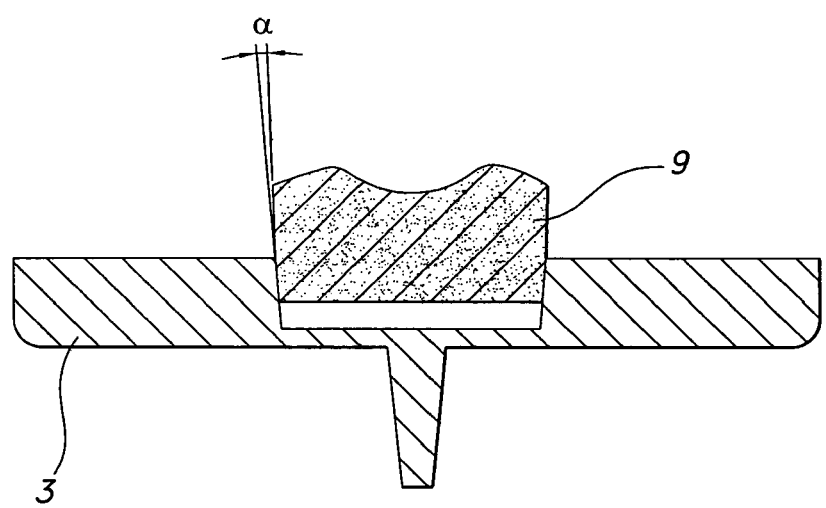
FIG. 10 shows a sectional view in the frontal plane in a support body with a conical clamping mounting assembly.
Figure 11:
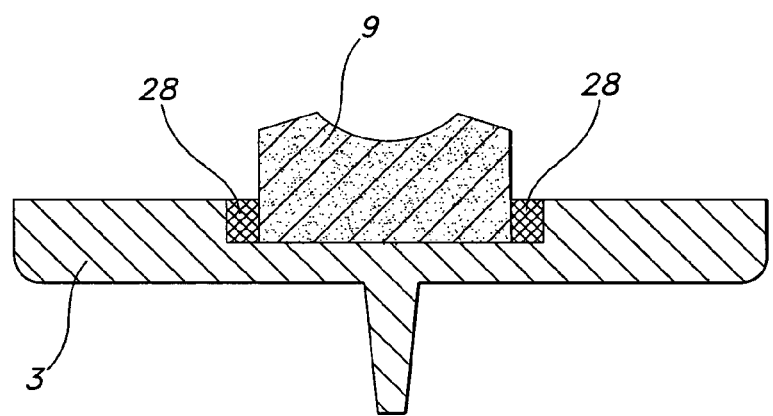
FIG. 11 shows a sectional view in the frontal plane in a support body with an elastic intermediate element mounting assembly.
Figure 12:
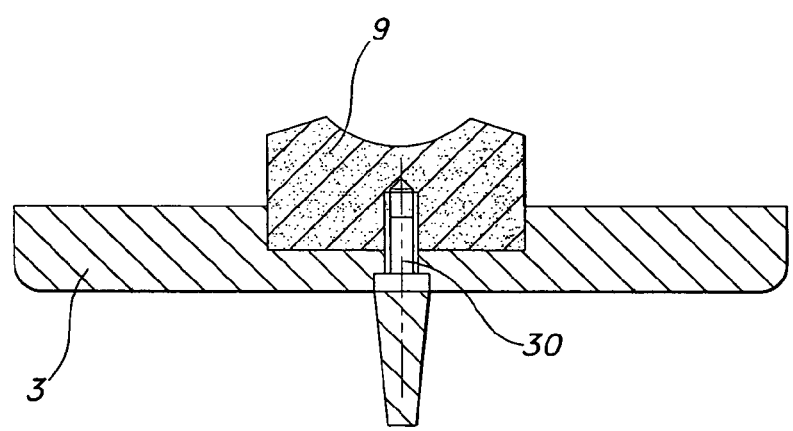
FIG. 12 shows a sectional view in the frontal place in a support body with a locking screw mounting assembly.

The components described above may be mounted substantially without clearance, because abrasion may otherwise occur at ceramic/metal interfaces because of the hardness of the ceramic material. This clearance-free mounting/assembly can be achieved, e.g., by means of a conical clamping, as illustrated in FIG. 10 (α helps depict the conical shape of joint body 9). However, other possibilities of the clearance-free mounting/assembly can be exhausted as well, such as: shrinking of the parts onto bearing surfaces by means of thermal expansion, as illustrated in FIG. 4; use of elastic intermediate elements (as illustrated in FIG. 11), which compensate a clearance between components due to their intrinsic elasticity/deformation; and additional locking screws 30, as illustrated in FIG. 12.

The intervertebral disk prosthesis can be inserted with the aid of navigated instruments. In use, components are assembled prior to implantation, and the intervertebral disk prosthesis is implanted in the assembled state, thereby significantly simplifying the implantation procedure.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed is:

1. An intervertebral implant comprising:
   an upper support body comprising a dorsal edge;
   a lower support body comprising a dorsal edge;
   a saddle joint comprising two pivot axes and two saddle-shaped joint surfaces in contact with one another rotated by 90° in relation to one another; and
   two joint bodies,
   wherein each of said joint surfaces is part of a respective one of said joint bodies, and each of said joint bodies is inserted into a respective one of said support bodies, at least one of said joint bodies is rotatable in relation to said respective support body receiving said joint body around a pivot axis extending transversely to said two pivot axes of said saddle joint,
   said upper and lower support bodies are supported pivotably in relation to one another via said saddle joint, and
   said joint surfaces are made of a ceramic material.

2. The implant of claim 1, wherein one of said joint surfaces is directed in an anterior-posterior direction and the other one of said joint surfaces is directed in a lateral direction.

3. The implant of claim 1, wherein said saddle joint is arranged between a middle portion of said support bodies and said dorsal edges of said support bodies.

4. The implant of claim 1, wherein each of said support bodies and its respective joint surface is made in one piece of a ceramic material.

5. The implant of claim 1, wherein at least one of said joint bodies is inserted into said respective support body without clearance.

6. The implant of claim 5, wherein at least one of said joint bodies is secured in said respective support body via a conical clamping.

7. The implant of claim 5, wherein at least one of said support bodies is shrunk onto said respective joint body.

8. The implant of claim 5, wherein at least one of said joint bodies is fixed at said respective support body by means of locking screws.

9. The implant of claim 5, wherein at least one of said joint bodies is fixed at said respective support body by means of elastic intermediate elements.

10. The implant of claim 1, wherein said rotatable joint body is received rotatably in a rotationally symmetrical recess of said support body.

11. The implant of claim 1, wherein said rotatable joint body comprises a bearing part secured rigidly in said support body, and a joint surface part rotatable around an axis of rotation.

12. The implant of claim 11, wherein a layer comprising a low-friction and/or wear-reducing material is arranged between said joint body and said support body and between said bearing part and said joint surface part.

13. The implant of claim 11, wherein said bearing part and said joint surface part are rotatably connected to one another via a central bearing journal.

14. The implant of claim 11, wherein said bearing part comprises a bearing shell, and said joint surface part is rotatably received in said bearing shell.

15. The implant of claim 1, wherein each of said joint surfaces comprises a radius between 4 mm and 7 mm.

16. The implant of claim 1, wherein said support bodies are made of titanium, a titanium alloy, or a chromium-cobalt alloy.

17. The implant of claim 1, wherein said support bodies are made of polyether ether ketone.

* * * * *